(12) United States Patent
Petit et al.

(10) Patent No.: US 9,498,505 B2
(45) Date of Patent: Nov. 22, 2016

(54) EMBELIA CONCINNA EXTRACT COMPRISING FLAVONOIDS IN COSMETIC AND PHARMACEUTICAL COMPOSITIONS (71) Applicant: BAYER CONSUMER CARE AG, Basel (CH)

(72) Inventors: Virginie Petit, Lons (FR); Eric Theron, Montardon (FR)

(73) Assignee: Bayer Consumer Care AG, Basel (CH)

( * ) Notice: Subject to any disclaimer, the term of this patent is extended or adjusted under 35 U.S.C. 154(b) by 0 days.

(21) Appl. No.: 14/394,268

(22) PCT Filed: Apr. 10, 2013

(86) PCT No.: PCT/EP2013/057477
§ 371 (c)(1),
(2) Date: Oct. 14, 2014

(87) PCT Pub. No.: WO2013/153108
PCT Pub. Date: Oct. 17, 2013

(65) Prior Publication Data
US 2015/0086662 A1 Mar. 26, 2015

(30) Foreign Application Priority Data

Apr. 11, 2012 (EP) .................................... 12290128

(51) Int. Cl.
| | | |
|---|---|---|
| A61K 36/00 | (2006.01) | |
| A61K 36/185 | (2006.01) | |
| A61Q 19/00 | (2006.01) | |
| A61K 8/97 | (2006.01) | |
| A61K 31/352 | (2006.01) | |
| A61K 31/7048 | (2006.01) | |
| A61K 45/06 | (2006.01) | |

(52) U.S. Cl.
CPC ............... *A61K 36/185* (2013.01); *A61K 8/97* (2013.01); *A61K 31/352* (2013.01); *A61K 31/7048* (2013.01); *A61K 45/06* (2013.01); *A61Q 19/005* (2013.01); *A61K 2800/75* (2013.01); *A61K 2800/805* (2013.01)

(58) Field of Classification Search
None
See application file for complete search history.

(56) References Cited

U.S. PATENT DOCUMENTS

2003/0105031 A1    6/2003   Rosenbloom

FOREIGN PATENT DOCUMENTS

| | | | |
|---|---|---|---|
| CA | 2683731 A1 | * | 10/2008 |
| IN | 200901065 | | 5/2009 |
| JP | 2001302528 | | 4/2000 |
| JP | 2005289922 A | * | 10/2005 |
| JP | 2007217396 | | 8/2007 |
| KR | 20100001167 A | | 6/2008 |
| KR | 20090029873 A | | 3/2009 |
| KR | 20110017599 A | | 2/2011 |
| WO | 2004/037184 A2 | | 6/2004 |

OTHER PUBLICATIONS

Manguro et al, Flavonol glycosides from the leaves of Embelia Keniensis. Journal of the Chinese Chemical Society (Taipei, Taiwan) (2005), 52(1), 201-208.*

Krishna et al, Wound healing activity of embelin isolated from the ethanol extract of leaves of Embelia ribes Burm. Journal of ethnopharmacology, (Feb. 12, 2007) vol. 109, No. 3, pp. 529-534.*

* cited by examiner

*Primary Examiner* — Qiuwen Mi
(74) *Attorney, Agent, or Firm* — Yonggang Ji (57) ABSTRACT

The present invention deals with an *Embelia* extract—preferably an extract from *Embelia concinna* titrated in flavonoids—, its process for preparation and its use in a cosmetical or pharmaceutical composition for the treatment of skin sensitivity, for the treatment of allergic reactions of the skin, for soothing and for the treatment of itching skin and for the regulation of inflammatory drifts in the skin.

8 Claims, 4 Drawing Sheets

EMBELIA CONCINNA EXTRACT COMPRISING FLAVONOIDS IN COSMETIC AND PHARMACEUTICAL COMPOSITIONS

The present invention deals with an *Embelia* extract—preferably an extract from *Embelia concinna* titrated in flavonoids—, its process for preparation and its use in a cosmetical or pharmaceutical composition for the treatment of skin sensitivity, for the treatment of allergic reactions of the skin, for soothing and for the treatment of itching skin and for the regulation of inflammatory drifts in the skin.

*Embelia* genus belongs to the Myrsinaceae family and consists of about 130 species including a large number of creeping or almost climbing tropical shrubs spread in tropical and subtropical areas from Africa to Pacific area. In Madagascar, 8 species can be found and all are endemic. Globally *Embelia* species are known in folk medicine for antihelmintic properties (*Embelia ribes* and *Embelia schimperi*). In terms of literature and for skin application, *Embelia ribes* is documented to be used for wound healing and *Embelia officinalis* for skin hydration and dryness. JP 2001302528 discloses *Embelia ribes* for the inhibition of 5α-reductase. In IN 200901065, *Embelia ribes* is also quoted among other plants for alleviation of various skin diseases. JP 2005289922 discloses *Embelia javanica* for skin bleaching thanks to anti-tyrosinase activity.

*Embelia concinna* (Baker) is endemic from Madagascar where it is called Tanterakala, Takasina or Sirahazo. This shrub becoming lianous at maturity can be found in forests between 1200 m and 2 000 m in altitude and is in flower from October to January. Leaves are alternate and numerous with thin petiole and elliptic or lanceolate limb, inflorescences is paniculate with small quadramer or pentamer flowers. In Madagascar, aerial part of *Embelia concinna* is used for antihelmintic and antihaemorraghic properties and more specifically leaves are used against ulcers, hyperuricemia and constipation.

The presence of the phytochemical typical markers in Myrsinaceae family—benzoquinone and saponosides—has been reported in *Embelia concinna*, with respectively embelin and pentacyclic triterpens (primulagenin A, embeliagenin). Other substances of interest like flavonoids were also highlighted in *Embelia* genus: more specifically quercetin, quercitrin, kaempferol and kaempferol-3-O-arabinoside were qualitatively identified in *Embelia concinna* (Thesis of A. Lhuillier, L'institut National de Polytechnique de Toulouse, 2007). However, a large number of potential actives remain unidentified in *Embelia*, so it is still unclear which actives contribute to which activity and to what extent. Furthermore, the described extraction methods are resource intensive and obtain only small yields rendering them unsuitable for industrial use.

Quercitrin

Quercetin

Kaempferol

Kaempferol-3-arabinoside

Flavonoids are widely distributed in plants fulfilling many functions including producing yellow or red/blue pigmentation in flowers and protection from attack by microbes and insects. Flavonoids have a widespread distribution in plants (more than 4000 natural flavonoids described to date), a great variety and a low toxicity. Flavonoids have been referred to as "nature's biological response modifiers" because of strong experimental evidence of their inherent ability to modify the body's reaction to allergens, viruses, and carcinogens. Some of them show anti-allergic, anti-inflammatory, anti-microbial and anti-cancer activity. They are also known for their anti-oxidant potential and potential interaction with mitochondria.

Quercetin is the most abundant of flavonoids. It is a plant-derived flavonol that can be found in fruits, vegetables, leaves and grains or as an ingredient in supplements, beverages or foods. Foods rich in quercetin include black and green tea, capers, apples, onion, red grapes, citrus fruit, tomato, broccoli and other leafy green vegetables and a number of berries. A large number of studies concern oral intake of quercetin or plants containing it for various usages, e.g. anti-oxidant, anti-cancer, anti-viral, anti-inflammation and anti-allergic as well as for the treatment or alleviation of heart disease, metabolic syndromes or for fibralgia treatments. Regarding allergy, publication mention activity via mast cells synthesis regulation, like reduction of histamine or inflammatory mediators' synthesis. For the skin, quercetin was mentioned in literature for various properties, such as anti-melanogenesis, anti-microbial and anti-oxidant activities, wound healing, anti-inflammatory activity (e.g. cyclooxygenase and lipoxygenase inhibition), UV-mediated skin damage prevention or anti-aging. Furthermore, in WO2004037184 quercitin has been claimed for reduction, treatment or partial prevention of reactive and inflammatory dermatoses and in KR20110017599 for use in pore size reduction.

Quercitrin is a glycoside formed from the flavonoid quercetin and the deoxy sugar rhamnose, extracted from the bark of the oak (*Quercus*) as a bitter citron-yellow crystalline substance used as a pigment. It can also be found in Tartary buckwheat (*Fagopyrum tataricum*), *Phyllanthus urinaria*, *Thodendron ponticum*, *Eryhtrospermum monticolum* and others. Quercitrin is known to be active in lipid peroxidation, oxidation prevention, inflammation modulation and hapten-induced inflammation reduction, oxidative stress protection, allergic airways disease prevention. JP2007217396 discloses Quercitrin or extract containing it as anti-inflammatory agent and painkiller and it is also mentioned in cosmetic composition for anti-aging (KR20100001167, KR20090029873). However, the isolation and purification of quercitrin is a cost intensive process leading to additional use of resources (solvents and energy) and to low yields.

Reactive and inflammatory dermatoses are non-contagious disorders of the skin whose causes, when known, are usually related to allergic or other immune reactions. These disorders may take the form of mild irritation; however, in more severe cases, reactive and inflammatory dermatoses may be painful and damaging conditions severely affecting the life quality of a patient.

Examples of reactive and inflammatory dermatoses include, without limitation, eczema, lichens, pruritic urticarial papules and plaques of pregnancy, allergic contact dermatitis, seborrheic dermatitis, atopic dermatitis, and psoriasis. Besides the widespread inflammatory status and the impairment of skin condition, pruritus is a common manifestation of these dermatologic conditions.

In the cosmetic field, skin reactivity and inflammation are considered to lead to skin redness, reactive and sensitive skin as well as skin discomfort or itch sensation. Sensitive skin or reactive skin can be considered as a condition that exhibits a reduced tolerance to environmental stress(es) such as UV irradiation, cold, wind exposure, dryness, (tabacco) smoke, irritant side effects of medicaments or cosmetics or the like. Despite an otherwise 'healthy' condition, 40% of population experience some skin discomfort sensation up to itch corresponding to neurosensitivity as well as redness linked to inflammation process. These phenomena are emphasized by skin dryness that enables enhanced penetration of external irritants, and pathogens.

The terms skin immune system (SIS) or SALT (skin associated lymphoid tissue) have been proposed to describe the components of the skin, excluding the regional lymph nodes, involved in skin defence towards external aggressions and allergen contact. The SIS contains two major components, the cellular and humoral. The cellular component comprises keratinocytes, epidermal dendritic cells (Langerhans cells), dermal dendritic cells, lymphocytes, tissue macrophages, mast cells, endothelial cells, and granulocytes. The humoral components include Immunoglobulins, complement components, fibrinolysins, cytokines, eicosanoids, neuropeptides, and antimicrobial peptides.

Histamine is a mediator contained in cells such as mast cells and basophils, which is released after degranulation during allergic reactions of IgE-mediated hypersensitivity or non-IgE-mediated hypersensitivity. Degranulation and histamine release can also be stimulated by non-allergenic urticating or stinging molecules. Such histamine release is responsible for the appearance of allergy reactions such as anaphylaxis, edema, pruritus (itch) or hives. Histamine has long been recognized as one of the most important mediators of inflammation, with its properties of vasodilatation and increased vascular permeability.

The mediators providing from the activation of phospholipase A2, particularly prostaglandin E2 (PGE2) and leucotrien B4 (LTB4), play a pivoting role in cutaneous inflammatory reactions. In intradermal injection, or in topic application, LTB4 induces the infiltration of neutrophils in the dermis and the formation of microabscess in the epidermis. This mediator also produces a vascular hyperpermeability, the adhesion of leucocytes to blood and can act in synergy with PGE2. It potentiates the release of IL17 in mouse. LTB4 also contributes to processes linked to inflammatory skin diseases (augmentation of the vascular permeability, formation of edema, infiltration of inflammatory cells) such as eczema, psoriasis, atopic dermatitis or acne.

Neuropeptides are synthetized by nerves ends and comprise a large family of regulatory molecules including tachykinins (e.g. Substance P), calcitonin gene-related peptide (CGRP), somatostatin, vasoactive intestinal peptide, pituitary adenylate cyclase-activating polypeptide and propiomelanocortin-derived peptides. Many investigations support a role of tachykinins during immune and inflammatory reactions via the peptide binding to tachykinin (neurokinin) receptors (NKRs) of immune cells like skin keratinocytes, endothelial cells, mast cells, fibroblasts, Merkel cells, and Langerhans cells.

In inflammatory skin diseases such as atopic dermatitis, an increased number of substance-P-expressing nerve fibers have been observed. Substance P was also found to stimulate the release of chemokines such as interleukin-8 (IL-8), proinflammatory cytokines such as tumor necrosis factor α (TNFα), histamine, leukotriene B4 and prostaglandin D2. In animal models of inflammation, Substance P was shown to modulate immediate type skin hypersensitivity reactions and to promote the induction of contact hypersensitivity (CHS).

Among the calcitonin peptides family, CGRP upon stimulation is released by sensory as well as autonomic neurons and modulates vasodilatation, plasma extravasation as well as several biological functions of epidermal as well as dermal cells. There is evidence that CGRP receptors are expressed on inflammatory cells such as monocytes, macrophages, mast cells and neutrophils as well as epidermal cells including keratinocytes, melanocytes and Langerhans cells. The expression of CGRP in the skin was found to be upregulated upon UV irradiation.

Upon stimulation by exogenous or endogenous trigger factors, besides neuropeptides release, sensitive C-fibers are capable of transporting the itch signal to the central nervous system. For instance, a number of substances (e.g. amines, prostaglandins)—after binding on the surface of chemosensitive nerve endings—induce firing of the axons. Burning pain, heat, and itch are transmitted through these slow-conducting unmyelinated C-fibers. These free nerve endings of cutaneous sensory C-nerve fibers—part of a dense network of highly specialized afferent sensory and efferent autonomic nerve branches present in skin—are located in the papillary dermis and epidermis.

Bidirectional crosstalk between the nervous and the immune systems are called neurogenic inflammation: induced neuropeptides by inflammation mediators and neuropeptide-receptor expressing inflammatory cells participate to intensify the inflammation cascades.

It is desirable that the mutual intensification would be restrained at an early stage through application of a respective compound that is capable of affecting both the nervous and/or the immune system.

The objective of the present invention is therefore to provide an alternative new advantageous compound, pharmaceutical composition or cosmetic composition for the treatment or alleviation of skin or mucous membrane diseases or disorders related to restraining the skin immune system as well as sensory nerve system reactions towards external stress and as a consequence to hinder neurogenic inflammation.

The invention thus relates to an *Embelia* leaf extract characterized in that it is obtained by the following process steps:

a. Extraction of the leaves with a polar solvent mixture of water and alcohol,
b. removal of the alcohol,
c. filtration
d. partial or entire removal of the solvent from the aqueous filtrate.

The invention further relates to an *Embelia* leaf extract characterized in that it is a liquid extract with 1% to 8% dry matter content in a water-glycerine blend.

The invention further relates to an *Embelia* leaf extract characterized in that it comprises flavonoids in an amount of more than 3% by weight with respect to the total dry plant extract, preferably more than 5%, most preferably more than 7%.

According to the invention the *Embelia* leaf extract is an *Embelia concinna* leaf extract.

In another embodiment of the invention the *Embelia* leaf extract is comprised in a cosmetic composition, preferably an *Embelia concinna* leaf extract is comprised.

A further embodiment of the invention is a pharmaceutical composition comprising the *Embelia* leaf extract, preferably comprising an *Embelia concinna* leaf extract.

In a preferred embodiment, the inventive extract or composition comprising the extract can be used in indications in which the extract's activity addresses neuromediators and pro-inflammatory mediators alleviation, more specifically histamin degranulation lessening, prostaglandins and leucotriens synthesis reduction and substance P and CGRP synthesis reduction.

Such indications are:
dermatological or topical indications: reactive dermatoses like eczema, exanthema, lichens, pruritic urticarial papules and plaques of pregnancy, purpura, allergic contact dermatitis, seborrheic dermatitis, atopic dermatitis, psoriasis and related symptoms like pruritus, oedema of the mucous membrane, allergic rhinitis, allergic conjunctivitis, hay fever, vaginal inflammation in association with fungal or bacterial infections
cosmetic applications: reactive and sensitive skin, redness issue, skin discomfort or itch sensation, skin or mucous membrane inflammation as well as skin or mucous membrane soothing activity.

A pharmaceutical composition according to the present invention comprises at least one active compound or drug destined for diagnosis or therapy. A pharmaceutical composition may influence the state or functioning of the body or affect the state or functioning of pathogens, parasites or xenobiotics with the aim of their removal. A pharmaceutical composition may also aim at substituting body compounds or fluids.

The pharmaceutical composition or cosmetic composition of the present invention can be administered in any form by any effective route, including, e.g., oral, parenteral, enteral, intravenous, intraperitoneal, topical, transdermal (e.g., using any standard patch), ophthalmic, nasally, local, non-oral, such as aerosal, inhalation, subcutaneous, intramuscular, buccal, sublingual, rectal, vaginal, intra-arterial, and intrathecal, etc. The person skilled in the art will easily judge on which administration to be either suitable for the pharmaceutical composition or for the cosmetic composition. They can be administered alone, or in combination with any ingredient(s), active or inactive. Preference is given to a topical administration.

The pharmaceutical composition or cosmetic composition of the present invention can be converted in a known manner into the usual formulations such as pharmaceutical or cosmetic compositions or compositions used as food supplement (i.e. according to the concept of "beauty from within") or medical device. These may be liquid or solid formulations e.g. without limitation normal and enteric coated tablets, capsules, pills, powders, granules, elixirs, tinctures, solution, suspensions, suppositories, syrups, solid and liquid aerosols, emulsions, pastes, creams, ointments, milks, gels, salves, serums, foams, shampoos, sticks or lotions.

Preference is given to a pharmaceutical or cosmetic composition in a form of an aqueous solution, a white or coloured cream, ointment, milk, gel, salve, serum, foam, shampoo, stick, cream, paste, or lotion.

The pharmaceutical composition or cosmetic composition of the present invention can be further combined with any other suitable additive or pharmaceutically or cosmetically acceptable carrier. Such additives include any of the substances already mentioned, as well as any of those used conventionally, such as those described in *Remington: The Science and Practice of Pharmacy* (Gennaro and Gennaro, eds, 20th edition, Lippincott Williams & Wilkins, 2000); *Theory and Practice of Industrial Pharmacy* (Lachman et al., eds., 3rd edition, Lippincott Williams & Wilkins, 1986); *Encyclopedia of Pharmaceutical Technology* (Swarbrick and Boylan, eds., 2nd edition, Marcel Dekker, 2002). These can be referred to herein as "pharmaceutically or cosmetically acceptable carriers" to indicate they are combined with the active drug or compound and can be administered safely to a subject for therapeutic or cosmetic purposes.

The dosage of the pharmaceutical composition or cosmetic composition of the present invention can be selected with reference to the other and/or the type of disease or disorder and/or the disease or disorder status in order to provide the desired therapeutic or cosmetic activity. These amounts can be determined routinely for a particular patient or person to be cosmetically treated, where various parameters are utilized to select the appropriate dosage (e.g., type of disease or disorder, age of patient, disease or disorder status, patient health, weight, etc.), or the amounts can be relatively standard and can be easily determined by a person skilled in the art.

The amount of the administered pharmaceutical composition or cosmetic composition can vary widely according to such considerations as the particular compound and dosage unit employed, the mode and time of administration, the period of treatment, the age, sex, and general condition of the patient or person to be treated, the nature and extent of the condition treated, the rate of drug or compound metabolism and excretion, the potential drug combinations and drug-drug interactions, and the like.

The pharmaceutical composition or cosmetic composition may comprise any amount of *Embelia* extract. Preference is given to a pharmaceutical composition or cosmetic composition comprising dry or liquid extract of *Embelia concinna* leaves as described below. The liquid extract may be present in an amount of from 0.01% to 5%, preferably from 0.1 to 2.5%, more preferably from 1% to 2% by weight of the total composition.

In another embodiment, the dry extract can be used as a powder in an amount of 0.001 to 0.5%, preferably 0.005 to 0.1%.

A further objective of the present invention is a method of treating skin sensitivity and skin reactivity.

Also an objective of the present invention is a method of cosmetic treatment of disorders related to skin immune system and skin sensory systems.

Another objective of the present invention is a method of treating diseases or disorders, especially skin or mucous membrane diseases or disorders, related to inflammation, neuromediators release, neurogenic inflammation, and preferably histamine degranulation, substance P and CGRP releases, PGE-2 and LTB-4 releases.

The pharmaceutical composition or cosmetic composition according to the invention is administered once or more, preferably up to three, more preferably up to two times per day. Preference is given to a topical administration.

Nevertheless, it may in some cases be advantageous to deviate from the amounts specified, depending on body weight, individual behaviour toward the active ingredient, type of pharmaceutical preparation and time or interval over which the administration is affected. For instance, less than the aforementioned minimum amounts may be sufficient in some cases, while the upper limit specified has to be exceeded in other cases. In the case of administration of relatively large amounts, it may be advisable to divide these into several individual doses over the day.

The pharmaceutical composition or cosmetic composition of the present invention can also be combined with at least one further active substance or plant extract e.g. substances or plant extracts usually employed for pharmaceutical, dermatological or cosmetic use.

Further active substances include but are not limited to desquamating and/or moisturizing agents, UV filtering or blocking agents, depigmenting or propigmenting agents, antiglycation agents, anti-inflammatory agents, anti-microbial agents, agents stimulating the synthesis of dermal, epidermal, hair or nail macromolecules and/or preventing the degradation thereof, agents stimulating the differentiation of keratinocytes, muscle relaxants, antipollution and/or anti-free radical agents, slimming agents, agents acting on the microcirculation, agents acting on the energy metabolism of the cells, tightening agents, agents preventing the loss or stimulating the growth of hair, agents preventing grey or white hair, or a mixture thereof. Preferably that combination is contained in a topically dermatological composition.

The pharmaceutical composition or cosmetic composition can also contain at least one additional agent effective in skin immune system and sensory system modulation.

In a preferred embodiment of the invention the pharmaceutical composition or cosmetic composition can also contain at least one additional topical anti-inflammatory agent selected from the group of ibuprofen, acetaminophen or aspirin, capsaicin, or cortisone.

In an embodiment of the invention the inventive extract or a pharmaceutical or cosmetic composition comprising the same is advantageously combined with at least one antihistaminic. Antihistaminics according to the invention may be selected from the group of ketotifen, thonzylamine, mepyramine, thenalidine, tripelennamine, chlorpyramine, promethazine, tolpropamine, dimetindene, clemastine, bamipine, loratadine, isothipendyle, diphenhydramine, diphenhydraminmethylbromide, chlorphenoxamine, pheniramine, diphenylpyraline, dioxopromethazine, dimenhydrinate, thiethylperazine, meclozine, azelastine, levocabastine, astemizole, mebhydroline, terfenadine, mequitazine, cetirizine, emedastine, mizolastine, olopatadine, epinastine and antazoline. Especially preferred antihistaminiks are bamipine, clemastine, chlorphenoxamine, azelastine, terfenadine, and loratadine.

In another embodiment of the invention the inventive extract or a pharmaceutical or cosmetic composition comprising the same is advantageously combined with at least one glucocorticoid. Glucocorticoids according to the invention can be selected from the group of triamcinolone, dexamethasone, hydrocortisone, hydrocortisonacetate, hydrocortisonbutyrate, hydrocortisonbuteprate, prednisolone, betamethasone, methylprednisolone, clobetasone, flumetasone, fluocortine, fluperolone, fluorometholone, fluprednidene, desonide, triamcinolone, alclometasone, dexamethasone, clocortolone, betamethasone, fluclorolone, desoximetasone, fluocinolonacetonide, fluocortolone, diflucortolone, fludroxycortide, fluocinonide, budesonide, diflorasone, amcinonide, halometasone, mometasone, methylprednisolonaceponate, beclometasone, hydrocortisonaceponate, fluticasone, prednicarbate, difluprednate, ulobetasole, clobetasole, halcinonide, medrysone, desonide, formocortale, rimexolone, mazipredone, flunisolide and tixocortole. Especially preferred are the glucocorticoids hydrocortisone, beclometasone-dipropionate, and dexamethasone.

In another embodiment of the invention the inventive extract or a pharmaceutical or cosmetic composition comprising the same is advantageously combined with at least one mast cell granulation inhibitor. Inhibitors of mast cell granulation, also called mast cell stabilizers, are substances that inhibit the release of histamins from the mast cells. Exemplary and preferred species of this substance class are cromoglicinic acid, spagluminic acid, nedocromile and lodoxamide.

In another embodiment of the invention the inventive extract or a pharmaceutical or cosmetic composition comprising the same is advantageously combined with at least one leukotrienereceptor antagonist. Leukotriene-receptor-antagonists are substances that inhibit the synthesis of leukotrienes and/or the interfere with the activity of the leukotrienes. Exemplary and preferred species of their substance class are montelukast, pranlukast, ibudilast and zafirlukast.

In another embodiment of the invention the *embelia* extract or the *embelia concinna* leave extract or a pharmaceutical or cosmetic composition comprising the same is combined with at least one further active ingredient which is selected from the group of phyto actives or plant extracts (e.g. evening primrose oil, borage oil, St. John's wort extract, aloe-vera extract, hamamelis extract, calendula extract, chamomille extract), Vitamines (e.g., vitamine E and its salts, tritinoine), dermatika (e.g. urea, heparine, hyaluronic acid, allantoine, lactic acid and its salts, pyroglutaminic acid, salicylic acid, tannins, coal tar solution, bisabolole, glycyrrhetinic acid and its salts, bitumino sulfates like e.g. Na-bitumino sulfonate or ammonium bitumino sulfonate, antibiotics (e.g. sulfonamide, erythromycin), antiseptics (e.g. clorhexidine or octenidine), local anaesthetics (e.g. lidocaine, polidocanole), decongestants (e.g. sympathomimetics such as xylometazoline), skin care substances (e.g. jojoba oil, aloe vera, lanoline, vegetable oils and fats) and light protectants (UV-A and -B filters, broad filters). Especially preferred is the combination with an anti-inflammatory compound or compound mix such as e.g. coal tar solution, Na-bitumino sulfonate, ammonium bitumino sulfonate, tretinoine, evening primrose oil, borage oil, St. John's wort extract, aloe-vera extract, hamamelis extract, calendula extract, chamomille extract, vitamine E and its salts, bisabolole, allantoine, glycyrrhetinic acid and its salts as well as polidocanole.

In the cosmetic field, skin reactivity and inflammation are considered to lead to skin redness, reactive and sensitive skin as well as skin discomfort, itch sensation, overheating, or tingling sensations of tightness. Sensitive skin or reactive skin can be considered as a condition that exhibits a reduced tolerance to environmental stress(es) such as UV irradiation, temperature, climate, air pollution or (tabacco) smoke, irritant side effects of medicaments, cosmetics or chemicals, xenobiotics, compounds capable of peeling, or a skin reaction induced by friction on the skin, mucous membranes or scalp. Compounds that are able to alleviate said conditions are called soothing.

In an embodiment of the invention, the inventive extract or a cosmetic composition comprising the same is used as a cosmetic soothing agent.

In another embodiment of the invention, the inventive extract or a cosmetic composition comprising the same is used in a method of cosmetic treatment of skin redness, reactive and sensitive skin as well as skin discomfort, itch sensation, overheating, or tingling sensations of tightness by applying the same topically onto the respective skin, mucous membrane or scalp.

According to another embodiment of the invention the inventive extract or a pharmaceutical or cosmetic composition comprising the same are used to alleviate the action of active ingredients with an irritant side effect that are thus likely to cause skin irritation, especially in persons with sensitive skin. As active ingredients that are likely to have an irritant side effect, the following may be cited, for example: keratolytic agents such as α-hydroxy-acids like glycolic, lactic, malic, citric, tartaric, mandelic acids and their derivatives; α-hydroxy-acids like salicylic acid and its derivatives; α-keto-acids like ascorbic acid or vitamin C and its derivatives; retinoids like retinol and its esters, retinal, retinoic acid and its derivatives; minoxidil and its derivatives; lithium salts; hair tints or dyes like para-phenylenediamine (p-PDA) and some of its derivatives such as N-phenyl p-PDA and toluene 2,5-diamine sulfate; meta-phenylene diamine (m-PDA) and some of its derivatives such as toluene 3,4-diamine; ortho-phenylene diamine (o-PDA); alcoholic fragrancing solutions (perfume, eau de toilette, after shave, deodorant); anti-perspirant agents (certain aluminum salts); depilatory or permanent active ingredients (thiols, ammonium hydroxide); depigmenting agents (hydroquinone): anti-lice active ingredients; detergent (ionic and non-ionic) agents; and their mixtures.

For the cosmetic treatment of sensitive skin, so called soothing agents may be combined with the inventive extract or a pharmaceutical or cosmetic composition comprising the same. Soothing agents according to this invention are selected from the group of bisabolol, allantoin, menthol, sucrose, centella extract, especially glycosylated molecules, glycyrrhiza extract, farnesol, achillea millefolium extract, ruscus extract, malva extract, jasminum extract, rosmarinic acid and plant extract containing it, hamamelis extract and others as known by the person skilled in the art.

The invention further comprises a process for preparing *Embelia* extracts. According to the invention these extracts are of plants of the *Embelia* genus which include but are not limited to *Embelia concinna*.

The extraction can be performed on all parts of the plant(s). Preferably the leaves of a plant of the genus *embelia* is extracted. In another preferred embodiment *Embelia concinna* are extracted especially preferred the leaves of the *Embelia concinna* are extracted.

The extraction can be done by standard extraction methods. Preferably the extraction is carried out with a polar solvent applicable for extraction. Leaves are first extracted with a polar solvent, e.g. mixtures of water and alcohol, optionally several times. The obtained solution is then mixed, the alcohol is removed and the precipitate is removed by filtration. In another embodiment of the invention the whole polar solvent is removed and the residue is extracted with water. The obtained polar phase can optionally be further extracted with a non-polar solvent e.g. ethyl acetate or heptane to remove the waxes, essential oils, pigments and most of the non-polar molecules. After phase separation the solvent of the remaining polar phase is removed in order to obtain an extract—in powder or liquid form—containing flavonoids.

Optionally the extract can be dried by adding water and conducting a freeze-drying or adjusted by solvents added to consider a specific final medium and specific dry matter content. A process for preparing a *Embelia* leaf extract, preferably an *Embelia concinna* leaf extract, comprises the steps of a. Extraction of leaves with a polar solvent mixture of water and alcohol,
b. removal of the alcohol,
c. filtration
d. partial or entire removal of the solvent from the aqueous filtrate.

The polar solvent used for extraction is preferably alcohol or a mixture of water and alcohol wherein the alcohol is preferably ethanol. The ratio of the volume between water and alcohol can be from 50:50 up to 90:10, preferably 70:30.

The final step is the partial or entire removal of the solvent from the aqueous filtrate in order to either obtain a liquid form or a powder form. Preference is given to a liquid form with targeted dry matter content between 1% and 10% in a solvent, preferably 2 to 8%, most preferably 6 to 8% by weight. Solvent is preferably a water-glycerine blend: the ratio of the volume between water and glycerine can be from 25:75 up to 75:25, preferably 50:50.

The invention further comprises a *Embelia concinna* leaf extract. The extract according to the invention can be prepared as described above or as disclosed in Example 1.

An extract according to the invention is normally a liquid extract. Nevertheless the extract can also be used as powder, i.e. that the final adjustment step of the described extraction process is omitted or further proceeded, for instance by freeze-drying or atomisation or any method to get powder form, or is mixed with other active compounds or being incorporated in an optimized carrier like encapsulation.

A powder extract according to the invention can also be redissolved to obtain a liquid extract with predetermined dry matter content. In an embodiment of the invention the powder is redissolved in a water-glycerine blend: the ratio of the volume between water and glycerine can be from 25:75 up to 75:25, preferably 50:50.

Preference is given to a liquid plant extract containing flavonoids in an amount of more than 3% by weight with respect to the total dry plant extract, preferably more than 5%, most preferably between 7%. In a preferred embodiment of the invention the dry plant extract comprises the molecules quercitrin, quercetin and Kampferol-3-O-arabinoside in an amount of 0.0001%-20%, whereby quercitrin may be present in an amount of 0.01% to 10%, preferably 0.05 to 8%, most preferably 2 to 5% by weight, quercetin in an amount of 0.001% to 1%, preferably 0.005 to 0.1%.

The invention further comprises the use of the *Embelia* extracts, especially *Embelia concinna* extracts, preferably *Embelia concinna* leaf extract in the modulation of sensory system and immune system reactions, especially in the inhibition and/or reduction of histamine and/or substance P and/or CGRO and/or prostaglandins and/or leucotrienes synthesis. It further comprises the use of the *Embelia* plant extracts for the treatment of skin diseases or disorders or mucous membrane diseases or disorder related to an enhanced level of inflammatory and neuropeptides mediators. It further comprises the use of the *Embelia* plant extracts as anti-inflammatory agent.

The invention is further described by the following examples.

EXAMPLES

Example 1

Extraction Process

Crushed dry leaves of *Embelia concinna* were extracted with a mixture of ethanol and water 70:30. The solution was stirred and heated below 60° C. during the extraction step. Extraction step was performed twice. After plant removal by filtration, ethanol was evaporated to obtain an aqueous solution.

Version A: Dry Extract

After settling, extract was filtered and was finally freeze-dried to get a powder form.

The final extract was characterized by thin layer chromatography (TLC) and spectrophotometry for flavonoids assay. The final composition showed by thin layer chromatography (solvents: ethyl acetate, acetic acid, formic acid, water (100:11:11:20 V/V/V/V)) the presence of quercetin, quercitrin & kampferol-3-O-arabinoside and a content of 7.5% of flavonoids. Additional investigation by HPLC led to titrate quercitrin and quercetin with respective quantity of 3.4% and 0.06%.

Version B: Liquid Extract/7% Solution

Same protocol can be proceeded with adapting the last step to get a liquid form. After extract filtration, adjustment was possible by adding glycerin to target a 7% extract in a water-glycerin blend 50/50 (v/v). Test in this protocol enabled to get a dry matter content of 7.3% extract (73 g/L).

Example 2

Cosmetic Composition

TABLE 1

Emulsion comprising *Embelia* extract

| | Ingredients/INCI | % (w/w) |
|---|---|---|
| A | Beheneth-10 | 1.5% |
| | Beheneth-25 | 1.5% |
| | Dycaprylyl Carbonate | 5.0% |
| | Hexyl Laurate | 5.0% |
| | Isohexadecane | 5.0% |
| | Cetearyl Isononanoate | 5.0% |
| | Dimethicone | 1.0% |
| | Behenyl Alcohol | 2.0% |
| | Hydrogenated Vegetable Glycerides | 2.0% |
| | Tocopheryl Acetate | 0.5% |
| | Preservative | qs |
| B | Water | qsp 100 |
| | Glycerin | 3.0% |
| | Xanthan gum | 0.1% |
| | Carbomer | 0.2% |
| C | *Embelia* extract (Liquid extract according to example 1) | 2% |

Ingredients A and ingredients B are heated separately to 80° C. They are then mixed under vigorous stirring. The stirring is reduced to gentle stirring while cooling to room temperature. Ingredient C is added below 40° C.

TABLE 2

Cream comprising *Embelia* extract

| | Ingredients/INCI | % (w/w) |
|---|---|---|
| A | Water | 72.12 |
| | Acrylate/C10-30 Alkyl Acrylate Crosspolymer | 0.20 |
| | Glycerin | 6.00 |
| B | Xanthan gum | 0.3 |
| | Cyclopentasiloxane | 2.00 |
| C | Isostearyl Alcohol, Butylene Glycol Cocoate, Ethylcellulose | 4.00 |
| | Propylene Glycol Dipelargonate | 3.00 |
| | Caprylic/Capric Triglyceride | 3.00 |
| | Cyclopentasiloxane, Cyclohexasiloxane | 2.00 |
| D | Sodium hydroxide (10% solution) | 0.63 |
| E | *Embelia* extract (Liquid extract according to example 1) | 0.30 |

Ingredients A are mixed at room temperature. The ingredients of B and C are mixed separately at room temperature. The mixture of B is then added to that of A and vigorously stirred for 10 min before the mixture of C is added and further stirred for another 10 min. The mixture of D is added and as is finally E and the cream is stirred for another 5 min.

Example 3

Inhibition of Histamine Degranulation by Basophiles

Test was performed on liquid *Embelia* extract according to example 1 to measure its activity on degranulation of human basophils (KU812 cell line) stimulated with CP48/80. Effects on degranulation were evaluated by measuring histamine release after stimulation. Cells were cultured at 37° C., 5% $CO_2$ and culture medium concerned EBSS supplemented with $CaCl_2$ 1.8 mM, $MgCl_2$ 0.8 mM and Bovine serum albumine (BSA) 0.1%.

A preliminary cytotoxicity test to select doses for further assay was performed with viability test (MMT reduction assay and morphological observations) after 1 hour incubation.

KU812 cells were then seeded in culture medium containing or not (control) the test compound or the reference (cromoglycate at 10 mM) and cells were pre-incubated for 20 minutes. Cells were then stimulated or not (non-stimulated control) with histamine release inducer CP48/80 at 10 µg/ml and incubated for 20 minutes. All experimental conditions were performed in n=3. At the end of incubation, the quantity of histamine in culture supernatants was measured using an ELISA kit according to the supplier's instructions. The inter-group comparisons were performed by Student's t-test for data management.

Results are expressed in % according to the following formulas:

$$\text{Viability (\%)} = (OD\ \text{sample}/OD\ \text{control}) \times 100$$

$$\text{Inhibition (\%)} = \frac{\text{Stimulated Control's Mean} - \text{Value}}{\text{Stimulated Controls Mean} - \text{Non-stimulated Controls Mean}} \times 100$$

TABLE 3

Effect of extract on the viability of KU812 cells

| | Control | *Embelia* Extract Composition - Liquid extract according to example 1 with 7.3% of dry matter (% calculated as to refer to dry matter) | | | | | | | |
|---|---|---|---|---|---|---|---|---|---|
| | | 1.92E−05 | 0.000096 | 0.00048 | 0.0024 | 0.012 | 0.06 | 0.3 | 1.5 |
| Viability (%) | 102  102 | 98 | 98 | 96 | 94 | 87 | 92 | 28 | 33 |
|  | 100  96 | 94 | 95 | 92 | 90 | 85 | 92 | 24 | 23 |
|  | 98  100 | 90 | 84 | 85 | 83 | 83 | 89 | 33 | 54 |
| Mean | 100 | 94 | 92 | 91 | 89 | 85 | 91 | 28 | 36 |
| sem | 1 | 2 | 4 | 3 | 3 | 1 | 1 | 2 | 9 |
| Morphological observations | + | + | + | + | + | + | + | op | op |

Legend:
+: normal population;
+/−: growth reduction;
−: toxicity;
0: cells mortality
g: grains of compound;
op: opacity of the compound;
*: morphological modification;
ag: agglutinated cells
sem: Standard error of the mean (standard deviation divided by sample size square root)

TABLE 4

Effect of extract on histamine release from KU 812 cells

| | Treatment | | Basic data | | | | | | Normalized data | | |
|---|---|---|---|---|---|---|---|---|---|---|---|
| | Test compound | Concentration (calculated as to refer to dry matter) | Histamine (nM) | Mean Histamine (nM) | Sem (nM) | Stimulated Control (%) | Sem (%) | $p^{(1)}$ | Inhibition (%) | Sem (%) | $p^{(1)}$ |
| | Non-stimulated control | — | 12.9<br>12.4<br>12.7 | 12.7 | 0.1 | 31 | 0 | *** | 100 | 0 | *** |
| Stimulation with CP48/80 at 10 µg/ml | Stimulated control | — | 40.7<br>44.2<br>39.5 | 41.4 | 1.4 | 100 | 3 | — | 0 | 5 | — |
| | Cromoglycate | 10 mM | 32.3<br>27.0<br>29.0 | 29.5 | 1.6 | 71 | 4 | ** | 42 | 5 | ** |

TABLE 4-continued

Effect of extract on histamine release from KU 812 cells

| Test compound | Treatment Concentration (calculated as to refer to dry matter) | Basic data | | | | | | Normalized data | | |
|---|---|---|---|---|---|---|---|---|---|---|
| | | Histamine (nM) | Mean Histamine (nM) | Sem (nM) | Stimulated Control (%) | Sem (%) | $p^{(1)}$ | Inhibition (%) | Sem (%) | $p^{(1)}$ |
| Embelia Extract according to example 1 | 0.0024% | 18.6 12.5 20.9 | 17.4 | 2.5 | 42 | 6 | ** | 84 | 9 | ** |
| | 0.012% | 21.7 18.4 26.7 | 22.3 | 2.4 | 54 | 6 | ** | 67 | 8 | ** |
| | 0.06% | 29.8 52.4 30.6 | 37.6 | 7.4 | 91 | 18 | ns | 13 | 26 | ns |

Legend:
$^{(1)}$Threshold for statistical significance
ns: >0.05, Not significant
*: 0.01 to 0.05, Significant
**: 0.001 to 0.01, Very significant
***: <0.001, Extremely significant The results are visualized in FIG. 1. The treatment with compound 48/80, tested at 10 µg/ml, markedly stimulated histamine release from KU812 basophils and cromoglycate as a reference standard inhibitor, tested at 10 mM significantly inhibited this effect. These expected results validated this assay.

Figure 1:
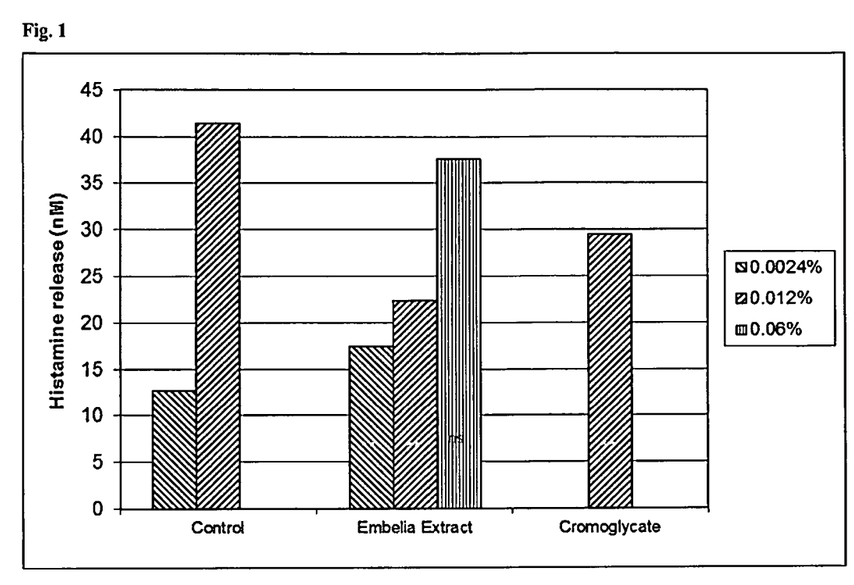
FIG. 1: Evaluation by Elisa assay of histamine release after induced basophils degranulation. Protocol: in vitro test on human basophils (KU812 cell line), pre-treatment with *Embelia* extract for 20 min, stimulation with CP48/80 (10 μg/ml) for 20 min, tested vs cromoglycate (10 nM) as standard reference.

Under the experimental conditions of this assay, *Embelia* extract according to example 1 inhibited the histamine release by degranulation of basophils.

Example 4

Inhibition of Histamine Degranulation by Mast Cells

Test was performed with liquid *Embelia* extract according to example 1 comprising 7.3% dry matter to measure its activity on degranulation of mast cells (Peritoneal cells from Wistar rat including ~50% mast cells) stimulated with CP48/80. Effects on degranulation were evaluated by measuring histamine release after stimulation. Cells were cultured at 37° C., 5% $CO_2$ and culture medium concerned EBSS supplemented with $CaCl_2$ 1.8 mM, $MgCl_2$ 0.8 mM and Bovine serum albumine (BSA) 0.1%.

Mast cells were seeded in culture medium containing or not containing (control) the test compound or the reference (cromoglycate at 10 mM) and cells were pre-incubated for 20 minutes. Cells were then stimulated or not stimulated (non-stimulation control) with histamine release inducer CP48/80 at 10 µg/ml and incubated for 20 minutes. All experimental conditions were performed in n=3. At the end of incubation, the quantity of histamine in culture supernatants was measured using an ELISA kit according to the supplier's instructions. The inter-group comparisons were performed by Student's t-test for data management.

Results are expressed in % according to the following formulas:

$$\text{Inhibition (\%)} = \frac{\text{Stimulated Control's Mean} - \text{Value}}{\text{Stimulated Controls Mean Non-stimulated Controls Mean}} \times 100$$

TABLE 5

Effect of extract on histamine release from mast cells

| | Test compound | Concentration (calculated as to refer to dry matter) | Mean Histamine (µM) | Stimulated Control (%) | $p^{(1)}$ | Normalized data Inhibition (%) | $p^{(1)}$ |
|---|---|---|---|---|---|---|---|
| | Control | — | 0.8 | 1 | *** | 100 | *** |
| Stimulation with CP48/80 at 10 µg/ml | Control | — | 58.3 | 100 | — | 0 | — |
| | Embelia Extract - according to example 1 | 0.0001% | 61.3 | 105 | ns | −5 | ns |
| | | 0.00048% | 40.0 | 69 | ns | 32 | ns |
| | | 0.0024% | 33.0 | 57 | nc | 44 | nc |
| | | 0.012% | 22.4 | 38 | ** | 63 | ** |

TABLE 5-continued

Effect of extract on histamine release from mast cells

| Test compound | Concentration (calculated as to refer to dry matter) | Mean Histamine (μM) | Stimulated Control (%) | p[1] | Normalized data Inhibition (%) | p[1] |
|---|---|---|---|---|---|---|
| | 0.03% | 3.0 | 5 | *** | 96 | *** |
| | 0.06% | 0.4 | 1 | *** | 101 | *** |
| Cromoglycate | 10 mM | 11.7 | 20 | *** | 81 | *** |

Legend:
[1]Threshold for statistical significance
ns: >0.05, Not significant
*: 0.01 to 0.05, Significant
**: 0.001 to 0.01, Very significant
***: <0.001, Extremely significant
nc: not calculable The treatment with compound 48/80, tested at 10 μg/ml, markedly stimulated histamine release from KU812 basophils and cromoglycate, tested at 10 mM significantly inhibited this effect. These expected results validated this assay.

Figure 2:
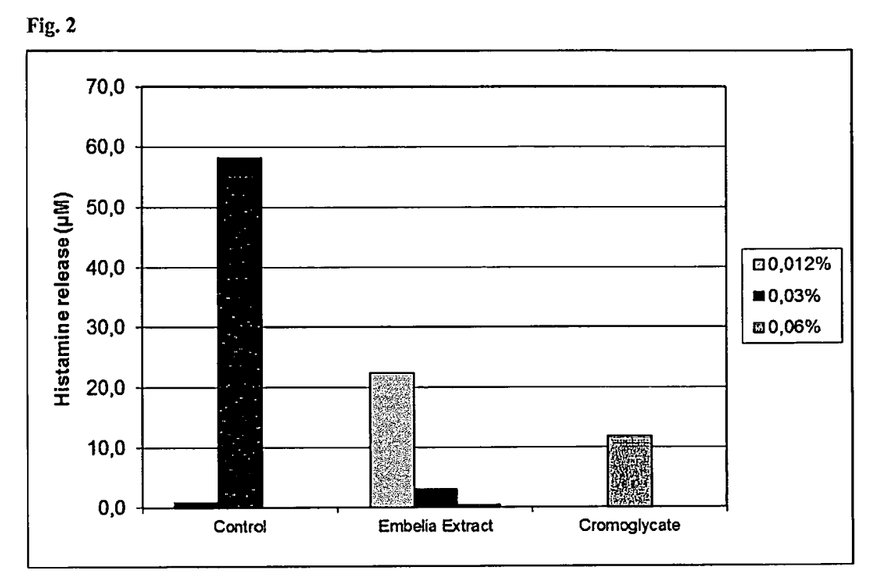
FIG. 2: Evaluation by Elisa assay of histamine release after induced mast cells degranulation. Protocol: in vitro test on mast murine cells, peritoneal cells from Wistar rat including ~50% mast cells, re-treatment with *Embelia* extract for 15 min, stimulation with CP48/80 (10 μg/ml) for 20 min, tested vs cromoglycate (10 nM) as standard reference.

Under the experimental conditions of this assay, *Embelia* extract according to example 1 showed a concentration-dependent inhibition of induced histamine release by mast cells. The results of table 5 are visualized in FIG. 2.

Example 5

Reduction of Substance P and CGRP Release by Nerves

Test was performed with liquid *Embelia* extract according to example 1 to measure its activity on release of substance P or CGRP induced by capsaicin in sensory neurons models. Cells were isolated from dorsal root ganglia of newborn Wistar rat. Cells were cultured at 37° C., 5% $CO_2$ and culture medium concerned DMEM-Ham F12 supplemented with $N_2$ complement 1%, antibiotics, L-glutamine 2 mM, nerve growth factor beta 20 ng/ml, neutrophin 5 ng/ml.

A preliminary cytotoxicity test to select doses for further assay was performed with viability test (MMT assay).

Sensory neurons were then seeded in culture medium containing or not containing (control) the test compound or the reference (capsazepine at 30 μM) and cells were pre-incubated for 30 minutes. Cells were then stimulated or not stimulated (non-stimulation control) with capsaicin (a pungent and irritating agent from hot chili pepper) at 0.3 μM and incubated for 30 minutes. All experimental conditions were performed in n=3. At the end of incubation, the quantity of neuromediators (Substance P or CGRP) in culture supernatants was measured using respective ELISA kit according to the supplier's instructions. The inter-group comparisons were performed by Student's t-test for data management.

Results are expressed in % according to the following formulas:

$$\text{Viability (\%)} = (OD \text{ sample}/OD \text{ control}) \times 100$$

$$\text{Inhibition (\%)} = \frac{\text{Stimulated Control's Mean} - \text{Value}}{\text{Stimulated Controls Mean} - \text{Non-stimulated Controls Mean}} \times 100$$

TABLE 6

Effect of *Embelia* liquid extract on the substance P release + Viability results

| | Treatment | | Basic data | | | | | | Normalized data | | | Viability (MTT) % |
|---|---|---|---|---|---|---|---|---|---|---|---|---|
| | Test compound | Concentration (calculated as to refer to dry matter) | Substance P (pg/ml) | Mean Substance P (pg/ml) | Sem (nM) | % Stimulated Control (%) | Sem (%) | p[1] | Inhibition (%) | Sem (%) | p[1] | Stimulated Control |
| | Non-stimulated control | — | 13 24 21 | 19 | 3 | 8 | 1 | *** | 100 | 1 | *** | 118 |
| Stimulation with capsaicin (0.3 μM) | Stimulated control | — | 275 244 243 | 254 | 11 | 100 | 4 | — | 0 | 5 | — | 100 |
| | Capsazepine | 30 μM | 23 23 23 | 23 | 0 | 9 | 0 | *** | 99 | 0 | *** | 96 |
| | *Embelia* Extract - according to example 1 | 0.0024% | 141 155 112 | 136 | 13 | 54 | 5 | ** | 50 | 5 | ** | 109 |
| | | 0.012% | 47 60 61 | 56 | 5 | 22 | 2 | *** | 44 | 2 | *** | 110 |
| | | 0.06% | 41 | 44 | 2 | 18 | 1 | *** | 89 | 1 | *** | 132 |

TABLE 6-continued

Effect of *Embelia* liquid extract on the substance P release + Viability results

| Treatment | | Basic data | | | | | | Normalized data | | | Viability (MTT) % |
|---|---|---|---|---|---|---|---|---|---|---|---|
| Test compound | Concentration (calculated as to refer to dry matter) | Substance P (pg/ml) | Mean Substance P (pg/ml) | Sem (nM) | % Stimulated Control (%) | Sem (%) | p(1) | Inhibition (%) | Sem (%) | p(1) | Stimulated Control |
| | | 43 | | | | | | | | | |
| | | 49 | | | | | | | | | |

Legend:
(1)Threshold for statistical significance
ns: >0.05, Not significant
*: 0.01 to 0.05, Significant
**: 0.001 to 0.01, Very significant
***: <0.001, Extremely significant
Nc: not calculable

TABLE 7

Effect of *Embelia* liquid extract on CGRP release + Viability results

| | Treatment | | Basic data | | | | | | Normalized data | | | Viability (MTT) |
|---|---|---|---|---|---|---|---|---|---|---|---|---|
| | Test compound | Concentration (calculated as to as to refer to dry matter) | CGRP (pg/ml) | Mean CGRP (pg/ml) | Sem (nM) | Stimulated Control (%) | Sem (%) | p(1) | Inhibition (%) | Sem (%) | p(1) | Stimulated Control (%) |
| | Non-stimulated control | — | 105<br>15<br>120 | 80 | 33 | 5 | 2 | *** | 100 | 2 | *** | 116 |
| Stimulation with capsaicin (0.3 μM) | Stimulated control | — | 1741<br>1365<br>1802 | 1636 | 137 | 100 | 8 | — | 0 | 9 | — | 100 |
| | Capsazepine | 30 μM | 671<br>698<br>557 | 642 | 43 | 39 | 3 | ** | 64 | 3 | ** | 114 |
| | *Embelia* Extract - according to example 1 | 0.0024% | 2091<br>2153<br>1502 | 1915 | 208 | 117 | 13 | ns | −18 | 13 | ns | 104 |
| | | 0.012% | 2172<br>2186<br>1745 | 2034 | 145 | 124 | 9 | ns | −26 | 9 | ns | 100 |
| | | 0.06% | 361<br>292<br>322 | 325 | 20 | 20 | 1 | *** | 84 | 1 | *** | 110 |

Legend:
(1)Threshold for statistical significance
ns: >0.05, Not significant
*: 0.01 to 0.05, Significant
**: 0.001 to 0.01, Very significant
***: <0.001, Extremely significant The treatment with the inducer, capsaicin tested at 0.3 μg, significantly stimulated both substance P and CGRP release in neuron supernatants and capsazepine, tested at 30 μM significantly inhibited this effect. These expected results validated this assay.

Figure 3:
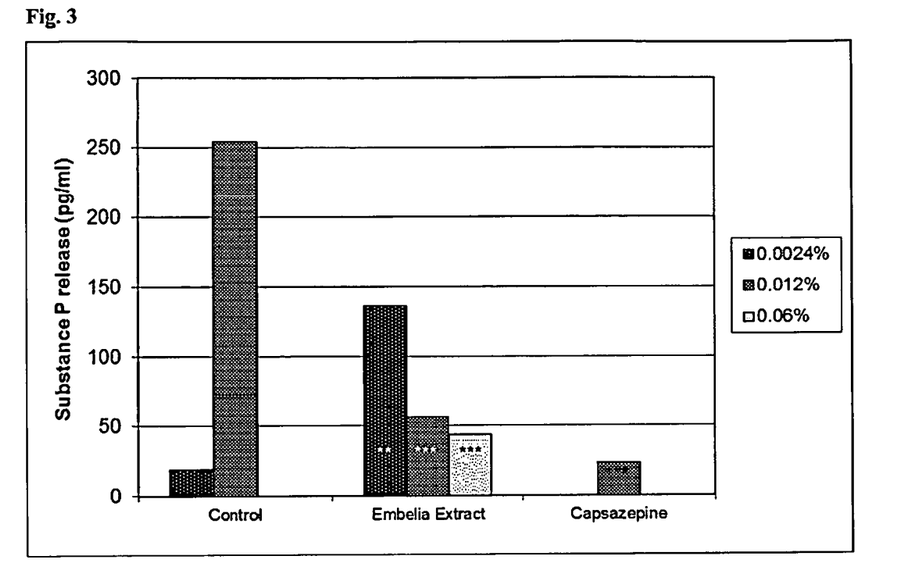
FIG. 3: Evaluation by Elisa assay of substance P release. Protocol: in vitro test on sensory neurons, sensory neurons from dorsal root ganglia of newborn Wistar rat, pre-treatment with *Embelia* extract for 30 min, stimulation with capsaicin (0.3 μM) for 30 min, tested vs capsazepine (30 μM) as standard reference.
Figure 4:
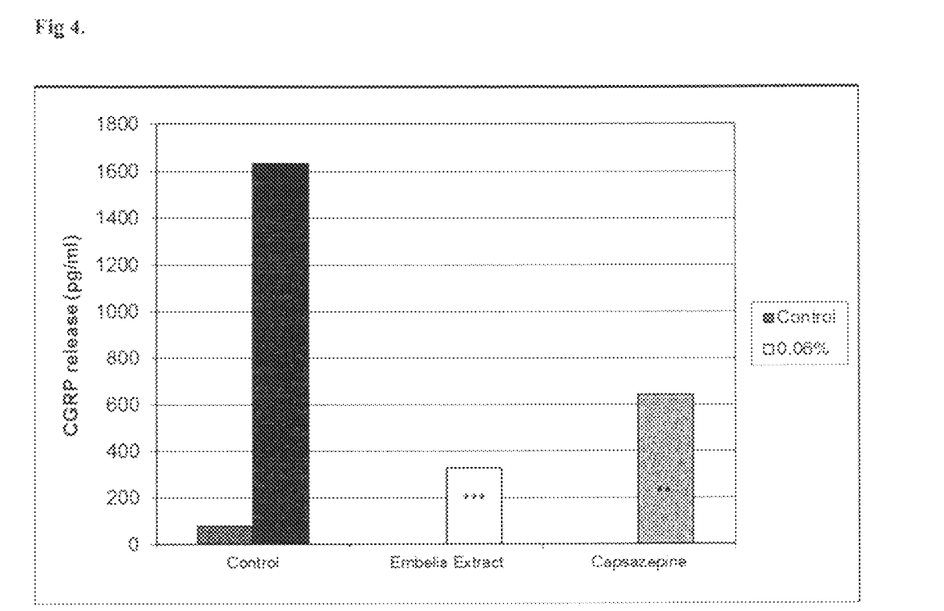
FIG. 4: Evaluation by Elisa assay of CGRP release. Protocol: in vitro test on sensory neurons, Sensory neurons from dorsal root ganglia of newborn Wistar rat, pre-treatment with *Embelia* extract for 30 min, stimulation with capsaicin (0.3 μM) for 30 min, tested vs capsazepine (30 μM) as standard reference.

Under the experimental conditions of this assay, *Embelia* extract according to example 1 inhibited significantly and dose-dependently the substance P released by sensory neurons and inhibited at the highest concentration tested the CGRP release. The tests with the two lowest *Embelia* extract concentrations did not yield any significant results and must be considered to be subcritical. The results of table 6 are visualized in FIG. 3 and those of table 7 in FIG. 4.

Example 6

Inhibition of Prostaglandin & Leucotrien Synthesis

The purpose of this study is the evaluation of the dry *Embelia* extract on the production of LTB4 (leucotriens B4) and PGE-2 (prostaglandin E-2) in human neutrophils.

Venous blood from healthy donors was collected into tubes containing anticoagulant and sedimented with Dextran (Dextran T500). The supernatant was layered on Ficoll-Hypaque (density 1,077) and centrifuged at 400 g for 20 min. The cell pellet was washed in Tyrode (in mM: NaCl 137; KCl 2.6; glucose 5.6; HEPES 4.2; pH 7.4). Contaminating red blood corpuscules were lyzed. The cells were resuspended at 2.106 cells/ml in the Tyrode buffer supplemented with $CaCl_2$ and $MgCl_2$ (1.3 and 1 mM, respectively).

Cells were treated with ECC at 50 μg/ml and 10 μg/ml during 25 minutes and cell viability was evaluated with the test of exclusion of trypan blue.

Cells (2.106 cells/ml) were incubated at 37° C. in the presence or absence of the products to be tested during 15 min and then stimulated with opsonised zymosan (1 mg/ml) during 10 min.

LTB4 assay was performed using a kit ELISA (Thermo Fisher ref. EHL LTB4). The quantity of LTB4 was expressed in pg/ml. PGE2 assay was performed using a kit ELISA (Assay designs ref 900-001 and SPIBIO ref 514010). The quantity of PGE2 was expressed in pg/ml.

Data represent the means of values measured in one supernatant (non stimulated cells) or three supernatants (stimulated cells). Each measurement was assessed in duplicate.

The means of the data were compared to the control condition (Student's t test-comparison of means—statistical significance at 95% if p<0.05* and at 99% if p<0.01**).

The percentage of inhibition was calculated as follows:

% inhibition=100×[(LTB4 treated with ECC (stimulated)/LTB4 control (stimulated)×100]

*Embelia* dry extract was not cytotoxic up to 50 μg/ml. Thus, the effects of 50 μg/ml, 5 μg/ml and 0.5 μg/ml on LTB4 release were investigated.

TABLE 8

Effect of *Embelia* dry extract on $LTB_4$ release

| | | $LTB_4$ (pg/ml) | SD |
|---|---|---|---|
| Control | (NS) | 16-ND | |
| | (S) | 963.3 | 118.9 |
| 50 μg/ml | (NS) | 24 | 0 |
| | (S) | >12000 | |
| 5 μg/ml | (NS) | ND-ND | |
| | (S) | 643.3 | 40.8 |
| 0.5 μg/ml | (NS) | 16 | 4.9 |
| | (S) | 1086.7 | 325.6 |
| Metronidazole (10 μg/ml) | (S) | 530 | 46.9 |

Legend: (NS): Not stimulated,
(S): Stimulated,
* p < 0.05,
** p < 0.01

At the concentration of 5 μg/ml, *Embelia* dry extract inhibited this release by 33% as compared with the untreated cells, p<0.05. Boswellic acid (10 μg/ml) and metronidazole (5 μg/ml) which are the positive controls of this experiment were inhibitory by 45% and 100% respectively.

TABLE 9

Effect of *Embelia* dry extract on $PGE_2$ release

| | | $PGE_2$ (pg/ml) | SD |
|---|---|---|---|
| Control | (NS) | 89 | 15.6 |
| | (S) | 158.7 | 16.9 |
| 5 μg/ml | (NS) | 76.5 | 19.1 |
| | (S) | 112.5 | 12.1 |
| 2.5 μg/ml | (NS) | 76 | 2.8 |
| | (S) | 127.7 | 17.6 |
| 1 μg/ml | (NS) | 89.1 | 15.5 |
| | (S) | 134.3 | 11.5 |
| Indomethacin 1 μM | (NS) | 60 | 8.5 |
| | (S) | 77.0 | 10.4 |

Legend: (NS): Not stimulated,
(S): Stimulated,
* p < 0.05,
** p < 0.01

*Embelia* dry extract inhibited the production of PGE2, dose-dependently and the inhibitory effect was significant at 5 μg/ml, 2.5 μg/ml and 1 μg/ml (% of inhibition: 29%, 20% and 15%, respectively). PGE2 release was inhibited by 51% with Indomethacin 1 μM (positive control).

The invention claimed is:

1. An *Embelia concinna* leaf extract characterized in that it comprises flavonoids in an amount of more than 3% by weight with respect to the total dry plant extract, further characterized in that it is a liquid in a water-glycerine blend form with 1% to 8% dry matter content.

2. The *Embelia* leaf extract according to claim 1 characterized in that it comprises quercitrin, quercetin and Kampferol-3-O-arabinoside in an amount of 0.0001%-20%, whereby quercitrin is present in an amount of 0.01% to 10% and quercetin in an amount of 0.001% to 1.

3. A cosmetic composition comprising the *Embelia* leaf extract according to claim 1.

4. A pharmaceutical composition comprising the *Embelia* extract according to claim 1.

5. The *Embelia* leaf extract according to claim 1 wherein the ratio of the volume between water and glycerine is from 25:75 up to 75:25.

6. The *Embelia* leaf extract according to claim 1 wherein the ratio of the volume between water and glycerine is about 50:50.

7. A method for the treatment of eczema, exanthema, lichens, pruritic urticarial papules, plaques of pregnancy, purpura, allergic contact dermatitis, seborrheic dermatitis, atopic dermatitis, psoriasis, pruritus, oedema of the mucous membrane, allergic rhinitis, allergic conjunctivitis, hay fever, vaginal inflammation in association with fungal or bacterial infections, or neurogenic inflammation of the skin or the mucous membranes, the method comprising the step of administering an effective amount of the *Embelia concinna* leaf extract according to claim 1 to the subject in need thereof.

8. A method for the treatment of reactive and sensitive skin, skin redness, skin discomfort or itch sensation, overheating or tingling sensation of tightness, skin inflammation comprising the step of administering an effective amount of the *Embelia concinna* leaf extract according to claim 1 to the subject in need thereof.

* * * * *